United States Patent

Jaaskelainen et al.

(10) Patent No.: US 9,566,580 B2
(45) Date of Patent: Feb. 14, 2017

(54) SEALED PIPETTE

(71) Applicant: THERMO FISHER SCIENTIFIC OY, Vantaa (FI)

(72) Inventors: Ari Jaaskelainen, Helsinki (FI); Mikael Lind, Helsinki (FI); Juha Telimaa, Jarvenpaa (FI); Aaro Tuominen, Espoo (FI)

(73) Assignee: THERMO FISHER SCIENTIFIC OY, Vantaa (FI)

( * ) Notice: Subject to any disclaimer, the term of this patent is extended or adjusted under 35 U.S.C. 154(b) by 149 days.

(21) Appl. No.: 13/970,722

(22) Filed: Aug. 20, 2013

(65) Prior Publication Data

US 2014/0056781 A1    Feb. 27, 2014

(30) Foreign Application Priority Data

Aug. 20, 2012  (FI) ...................... 20125861

(51) Int. Cl.
*B01L 3/02* (2006.01)
*B01L 3/00* (2006.01)
*G01N 35/10* (2006.01)

(52) U.S. Cl.
CPC ............ *B01L 3/0275* (2013.01); *B01L 3/0217* (2013.01); *B01L 3/021* (2013.01); *B01L 2200/02* (2013.01); *B01L 2200/025* (2013.01); *B01L 2400/0478* (2013.01); *G01N 35/1074* (2013.01); *Y10T 29/49826* (2015.01)

(58) Field of Classification Search
CPC ..... B01L 3/0275; B01L 3/021; G01N 35/1074
USPC ................................. 422/501, 511; D24/222
See application file for complete search history.

(56) References Cited

U.S. PATENT DOCUMENTS

| 8,202,495 | B1 | 6/2012 | Smith et al. |
| 2002/0041833 | A1* | 4/2002 | Telimaa et al. ............... 422/100 |
| 2003/0000319 | A1 | 1/2003 | Rainin et al. |
| 2006/0233669 | A1 | 10/2006 | Panzer et al. |
| 2008/0286157 | A1 | 11/2008 | Mathus et al. |
| 2009/0211332 | A1* | 8/2009 | Telimaa ........................ 73/1.74 |

(Continued)

FOREIGN PATENT DOCUMENTS

CN    101484242    7/2009

OTHER PUBLICATIONS

Search Report for FI 20125861 dated Dec. 6, 2013.
(Continued)

*Primary Examiner* — Jill Warden
*Assistant Examiner* — Brittany Fisher
(74) *Attorney, Agent, or Firm* — Nixon & Vanderhye P.C.

(57) ABSTRACT

The invention relates to liquid dispensing and concerns a pipette comprising at least one aspiration channel with a piston. At the lower end of the aspiration channel there is an extension channel (3) and at its end a pipette tip mounting piece (4) onto which a pipette tip (5) is attached. On the pipette tip mounting piece there is a surrounding groove (17) and in the groove a sealing ring (18). The width of the groove in the axial direction is at least 1.1 times the thickness of the sealing ring in the axial direction. When the mounting piece is pushed into the pipette tip, the inner wall of the tip can move the sealing ring upwards in the groove. The construction can provide a reliable sealing despite of inherent dimension differences between different tips and mounting pieces.

7 Claims, 3 Drawing Sheets

(56) References Cited

U.S. PATENT DOCUMENTS

Figure 1:
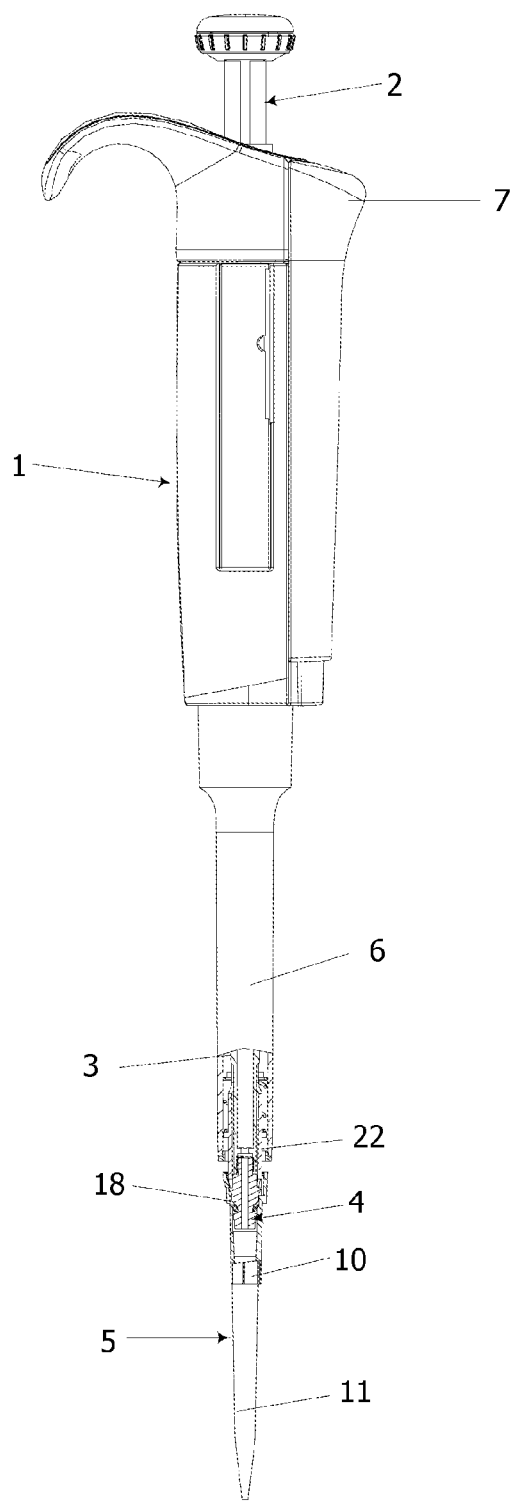

2010/0196210 A1     8/2010   Jungheim et al.
2010/0266453 A1*   10/2010   Rylski et al. ................. 422/100

OTHER PUBLICATIONS

European Search Report dated Oct. 31, 2013.
Communication pursuant to Article 94(3) EPC, EP Application No. 13180950.1-1402, May 20, 2016.

* cited by examiner

SEALED PIPETTE

TECHNICAL FIELD

The invention relates to liquid dispensing and concerns a pipette, in which a pipette tip is attached to the lower end of an elongated aspiration channel in which a piston is moved. The lower end of the channel is provided with a surrounding groove and a seal in the groove in order to secure that the tip is tightly attached.

TECHNICAL BACKGROUND

For liquid dispensing there are pipettes which comprise a piston by means of which liquid is aspirated into and removed from a pipette tip attached to an aspirating channel. The tip is sealed against the outer surface of the lower tip of the aspiration channel. The sealing is usually carried out so that the material of the tip is softer than that of the lower tip of the aspiration channel, whereby the tip yields and is thus sealed against the surface of the aspiration channel. The sealing may be carried out also, for example, by means of an O-ring in a surrounding groove on the outer surface of the aspiration channel. The width of the groove corresponds to the thickness of the O-ring. After dispensing, the tip is removed. For this, in the pipette there is usually a sleeve-like tip ejector, by means of which the tip is pushed off. In order to achieve reliable dispensing, the tip sealing must be sufficiently tight and proof so that the connection does not leak or the tip accidentally loosen. On the other hand, in order to achieve good usability and reliable operation of the tip remover, the forces needed for attaching and loosening should be as small as possible. Taking care of reliable sealing without increasing the release force too much is important especially in multichannel pipettes.

EP 2 452 754 describes a multichannel pipette in which the sealing has been carried out by means of an O-ring. The O-ring is placed in a groove the width of which in the axial direction corresponds to the thickness of the O-ring.

SUMMARY OF THE INVENTION

Now an invention in accordance with the claims has been made.

The invention concerns a pipette comprising an aspiration channel with a piston and at the lower end of the aspiration channel an extension channel with a pipette tip mounting piece. On the outer surface of the pipette tip mounting piece there is a surrounding groove and in the groove a sealing ring, for sealing the connection of the mounting piece and a pipette tip attached to the mounting piece so that the sealing ring seals the mounting piece against the pipette tip. The width of the groove in the axial direction is at least 1.1, preferably at least 1.2, more preferably at least 1.5, times the thickness of the sealing ring in the axial direction.

The shape of the lower surface and bottom of the groove preferably corresponds to the shape of the sealing ring. Thus, when the mounting piece is pushed into the pipette tip, the inner wall of the tip can move the sealing ring upwards in the groove. A suitable move distance is preferably 0.2-1 mm, such as 0.3-0.7 mm. The construction provides a reliable sealing despite of the inherent dimension differences between different tips and mounting pieces. This is especially useful in multichannel pipettes. In conventional multichannel pipettes dimension differences easily cause leakages in some channels and therefore harmfully big forces are often used to attach the tips. Additional differences in the attachment between different tips may be caused, when all the tips are taken at the same time from a row in a tip rack. The rack may be for example curved so that different mounting pieces push at different distances into the tips. The moving sealing ring is also advantageous when removing the tip, since the tip is less easily stuck to the sealing ring. This decreases the release forces needed and the wear of the sealing ring. The depth of the groove preferably decreases in the axial direction upwards. Then the friction between the sealing ring and the pipette tip may be made small in the beginning when the mounting piece is pushed into the tip. When the mounting piece is pushed further and the sealing ring is moved upwards in the groove, the ring is pressed tighter between the pipette tip and the piece thus ensuring a reliable sealing. Correspondingly, when the pipette tip is removed, the pipette tip is detached easily at the end of the removal. The upper surface of the groove may be e.g. planar.

The pipette tip preferably comprises at its upper part an inside extension with a bottom shelf. This bottom shelf is used to move the sealing ring upwards in the groove. The bottom shelf is preferably downwards sloping or horizontal.

According to one embodiment, only the friction force between the pipette tip and the mounting piece is used to attach the tip.

According to another embodiment, and additional attachment mechanism, especially a form closure mechanism, is used. This mechanism may be especially such as comprises attachment claws, e.g. such as described in US 2005/0175511, and EP 2 452 754. The moving sealing ring provides also a special advantage when attaching the pipette tip with the additional mechanism. Namely, when the mounting piece is pushed into the tip, the tip can move a little above the attachment position and then return down to the exact attachment position. This ensures that the tip reaches the required height on the mounting piece. This is an important advantage especially in multichannel pipettes.

In the claw mechanism, the pipette tip comprises at least one transversely resilient claw, preferably at least two claws. The claw is preferably a strip formed as an integral part of the tip. It may be especially such that its upper end is fixed on the jacket of the tip and the lower end is free. In its free state, the strip is bent inwards. The mounting piece comprises a flange, which, when the mounting piece is pushed into the tip, bends the tips outwards until the claw can again bend inwards on the upper surface of the flange. There is also a mechanism for opening the claws. It comprises a claw opener which, when pressed downwards, bends the claws outwards outside the edge of the flange and thus makes it possible to remove the tip.

The invention concerns also a method for sealing a pipette tip in a pipette, and a pipette tip.

DRAWINGS

Figures 2, 3:
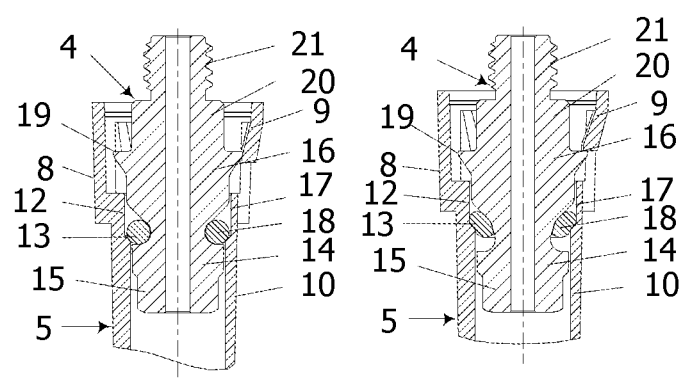
Figure 4:
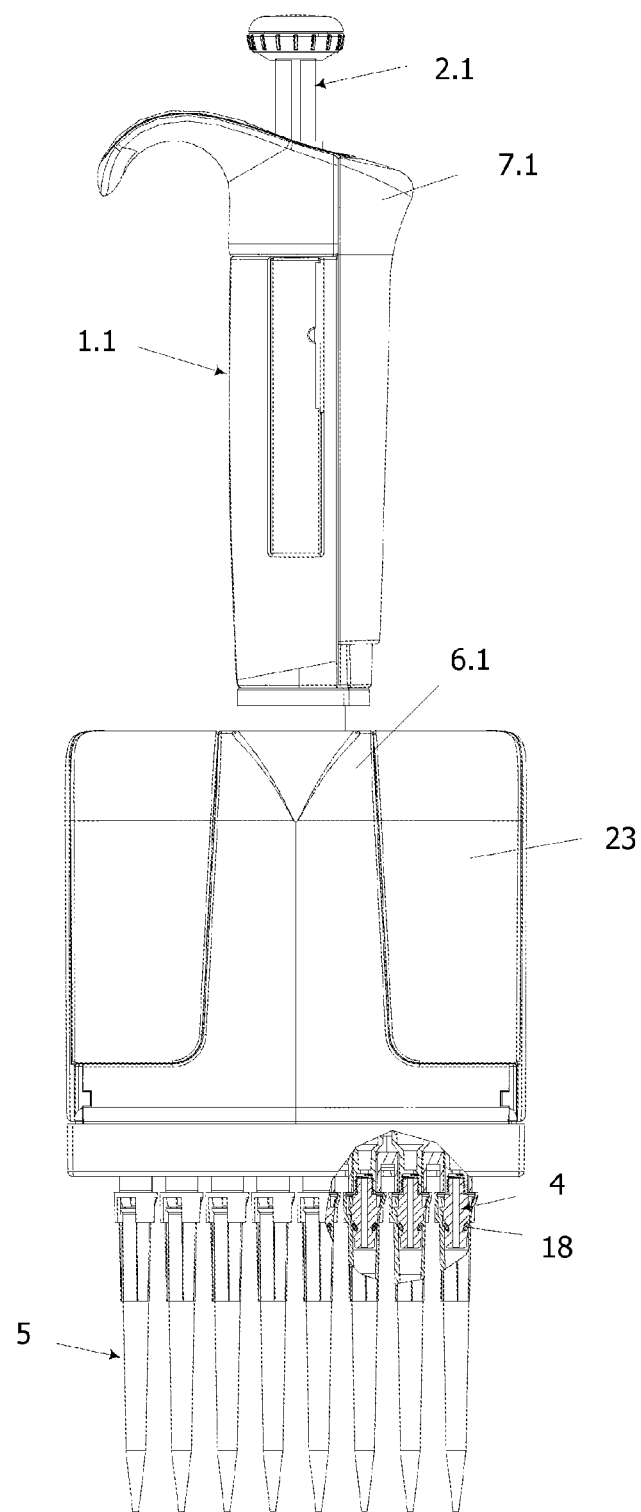

The enclosed drawings form a part of the written description of the invention and relate to the detailed description of some embodiments of the invention presented below. In the drawings, FIG. 1 shows a pipette from the front, FIG. 2 shows the lower end of the aspiration channel of the pipette of FIG. 1 and a pipette tip which is being pushed to the lower end, FIG. 3 shows the lower end of the aspiration channel and the pipette tip of FIG. 2 when the tip has been pushed on its place on the lower end of the channel, and FIG. 4 shows a multichannel pipette from the front.

DETAILED DESCRIPTION OF SOME EMBODIMENTS OF THE INVENTION

The pipette in accordance with the figures comprises a handle 1 and inside it a cylinder and a piston movable in it. The piston has an arm 2, the end of which extends out from the upper end of the handle. The arm is connected with a spring, which tends to press the piston to its upper position. The pipette comprises a volume adjustment mechanism, by means of which the stroke length of the piston and thereby the volume of the dispensed liquid can be adjusted by rotating the arm. The set volume is displayed on the side of the handle by digit rings. The cylinder comprises at its lower end an extension channel 3. At the lower end of the extension channel there is a pipette tip mounting piece 4 with an axial channel through it. A pipette tip 5 is attached onto the mounting piece. The mounting piece has been attached to the inside end of the channel by a thread. The pipette comprises also a pipette tip removing mechanism with a tip removal sleeve 6 sliding on the extension channel and a push button 7 on the side of the handle. These kinds of pipette mechanisms have been described e.g. in EP 112 887, EP 566 939, EP 737 515, WO 2005/050554, and EP 2 452 754.

The pipette tip 5 comprises a tubular body and a slightly conical broader mounting sleeve 8 at its upper end. The mounting sleeve comprises symmetrically three resilient locking claws 9. The claw is a resilient strip of the mounting sleeve. It extends downwards from the upper part of the mounting sleeve and its lower end is free. The length of the claw is a little less than half of the height of the mounting sleeve. When free, the claw is bent inwards. The body comprises an upper jacket 10 and a lower jacket 11. The wall thickness of the upper jacket is bigger than that of the lower jacket. The upper jacket comprises at its upper end an inside extension 12, the inside diameter of which is bigger than that of the lower part of the upper jacket. The inside extension comprises a downwards sloping (45°) bottom shelf 13.

The mounting piece 4 comprises a lower shaft 14. The width of its upper part is only slightly smaller than the inside diameter of the upper jacket 10 of the pipette tip so that shaft can slide into the upper jacket. The width of the lower part 15 of the lower shaft is essentially smaller than the inside diameter of the upper jacket. This structure facilitates pushing the lower shaft into the upper jacket. Above the lower shaft there is a middle shaft 16, the width of which is slightly smaller than the inside diameter of the extension 12 of the upper jacket so that the middle shaft can slide into the extension. Between the lower shaft and middle shaft there is a groove 17 for a sealing O-ring 18. The width of the groove (in the axial direction) is about twice the thickness of the O-ring. The surface of the lower part and bottom of the groove is rounded corresponding to the shape of the unpressed O-ring. The outside diameter of the O-ring is slightly smaller than the inside diameter of the extension of the upper jacket. When at the lower position in the groove, the O-ring is unbiased. The upper surface of the groove is planar. At the upper part of the middle shaft there is a wider flange 19, the upper surface which is planar. Above the flange there is a mounting shaft 20 and at the upper end a threading 21, by which the mounting piece is attached to the lower end of the extension channel 3.

When the pipette tip 5 is pushed onto the mounting piece, the lower shaft 14 of the mounting piece slides into the narrower part of the upper jacket 10, and the middle shaft slides into the extension 12. At the same time, the flange 19 bends the claws 9 outwards until they slip above the flange and bend back inwards along the upper surface of the flange and lock the tip firmly on the mounting piece 4. The mounting piece and the pipette tip are so dimensioned that, when the claws are against the upper surface of the flange, the shelf 13 has pushed the O-ring a little upwards so that it is now deformed and pressed tightly between the upper surface of the groove 17 and the wall of the extension of the upper jacket. This ensures a reliable sealing between the tip and the mounting piece. An additional advantage is that the sealing is always tight despite of inherent deviations inside the tolerances of the dimensions between different mounting pieces and tips. The O-ring only deforms more when it is moved a longer distance.

The tip removal mechanism of the pipette comprises a mechanism for opening the claws (see EP 2452 754). In this mechanism there is an opening sleeve 22 around the lower end of the extension channel 3. The lower end of the opening sleeve 6 extends below the lower end of the tip removal sleeve 6. When the button 7 is pushed, the opening sleeve moves downwards against the inside surface of the claws and forces them to bend outwards. When the claws are beyond the edge of the flange 19, the tip removal sleeve moves against the upper end of the tip and pushes the tip away from the mounting piece.

FIG. 4 shows an eight channel pipette. The pipette comprises a handle 1.1 and a housing 23 at the lower end of the handle. In the housing there are in a row eight cylinders with a piston. The pistons are connected with a common bar to an arm 2.1. On the side of the housing there is a tip remover 6.1 connected to a push button 7.1 on the side of the handle. The mechanism corresponds to that described in EP 2 452 754.

At the lower end of each cylinder there is a mounting piece 4, a pipette tip 5, and a sealing ring 18 in the same way as in the pipette of FIG. 1.

The invention claimed is:

1. A pipette comprising:
   At least one aspiration channel with a piston, the aspiration channel comprising a lower end,
   An extension channel formed as an extension at the lower end of the aspiration channel, the extension channel comprising a lower end,
   A pipette tip mounting piece formed at the lower end of the extension channel,
   A pipette tip attached to the pipette tip mounting piece,
   A surrounding groove formed on an outer surface of the pipette tip mounting piece, the groove comprising lower and upper surfaces and having a depth which decreases in an axial direction from the bottom surface thereof towards an upper end of the upper surface thereof so as to establish a region of decreased groove depth at the upper end of the upper surface thereof, and
   A single O-ring seal positioned for movement within the groove in the axial direction between the lower and upper surfaces thereof in response to the mounting piece being pushed into the pipette tip to cause the o-ring seal to thereby be pushed upwardly in the groove toward the upper end of the upper surface of the groove and be deformed in the region of decreased groove depth to establish a seal between the mounting piece and the pipette tip, wherein The groove has a width in an axial direction of the mounting piece which is at least 1.1 times a thickness of the o-ring seal in the axial direction.

2. The pipette according to claim 1, wherein the pipette tip comprises an upper part with an inside extension.

3. The pipette according to claim 1, wherein the pipette tip comprises at least one resilient claw.

4. The pipette according to claim 1, wherein the bottom surface of the groove is rounded and the upper surface of the groove is planar.

5. A method for mounting a pipette tip onto a pipette, the method comprising:
 (a) providing a pipette according to claim 1 and a tubular pipette tip to be mounted onto the pipette, and
 (b) pushing the mounting piece of the pipette into the tubular pipette tip to cause the O-ring seal to be moved upwardly in an axial direction of the pipette and into the region of deceased groove depth thereby deforming the O-ring seal against the upper surface of the groove and establishing a seal between the mounting piece and the pipette tip.

6. The method according to claim 5, wherein step (b) is practiced so as to upwardly move the sealing ring in the axial direction of the pipette a distance of 0.2-1 mm.

7. A pipette comprising:
 at least one aspiration channel with a piston, the aspiration channel comprising a lower end,
 an extension channel formed as an extension at the lower end of the aspiration channel, the extension channel comprising a lower end,
 a pipette tip mounting piece formed at the lower end of the extension channel,
 a pipette tip attached to the pipette tip mounting piece,
 a surrounding groove formed on an outer surface of the pipette tip mounting piece, the groove comprising a rounded bottom surface and a planar upper surface extending upwardly from the rounded bottom surface so as to establish a decreased groove depth in an axial direction from the bottom surface thereof towards an upper end of the upper surface thereof, and
 an O-ring seal positioned in a non-deformed state in the rounded bottom surface of the groove and movable within the groove in the axial direction between the rounded lower surface and the planar upper surface thereof in response to the mounting piece being pushed into the pipette tip to cause the O-ring seal to thereby be pushed upwardly in the groove toward the upper end of the planar upper surface of the groove and be deformed thereby in the region of decreased groove depth to establish a seal between the mounting piece and the pipette tip.

* * * * *